US006539939B2

United States Patent
Rubin

(10) Patent No.: US 6,539,939 B2
(45) Date of Patent: Apr. 1, 2003

(54) MULTI-FUNCTION ORAL BREATHING SUPPORT SYSTEM

(76) Inventor: Darren Rubin, 3844 Chaucer Way, Land O'Lakes, FL (US) 34639

(*) Notice: Subject to any disclaimer, the term of this patent is extended or adjusted under 35 U.S.C. 154(b) by 160 days.

(21) Appl. No.: 09/740,605

(22) Filed: Dec. 18, 2000

(65) Prior Publication Data

US 2002/0073995 A1 Jun. 20, 2002

(51) Int. Cl.[7] ............... A61M 16/00; A61M 15/00; B05D 7/14; B65D 83/06
(52) U.S. Cl. ............... 128/203.15; 128/203.12; 128/203.17; 128/200.23; 604/58
(58) Field of Search ............... 128/200.16, 200.18, 128/200.22, 200.23, 203.12, 203.14, 203.23, 203.24, 200.24; 239/338; 600/529, 533, 538, 539, 540, 541; 604/82, 83, 84, 85, 86, 58

(56) References Cited

U.S. PATENT DOCUMENTS

| | | | | |
|---|---|---|---|---|
| 2,431,649 A | * | 11/1947 | Moats | 128/203.24 |
| 3,584,621 A | * | 6/1971 | Bird et al. | 128/200.18 |
| 3,635,213 A | * | 1/1972 | LaHay | 119/14.14 |
| 4,041,935 A | * | 8/1977 | Garbe | 482/13 |
| 4,062,358 A | * | 12/1977 | Kritzer | 128/204.18 |
| 4,198,969 A | * | 4/1980 | Virag | 128/200.21 |
| 4,221,381 A | * | 9/1980 | Ericson | 482/13 |
| 4,403,616 A | * | 9/1983 | King | 482/13 |
| 4,444,202 A | * | 4/1984 | Rubin et al. | 482/13 |
| 4,454,877 A | * | 6/1984 | Miller et al. | 128/200.21 |
| 4,635,647 A | * | 1/1987 | Choksi | 482/13 |
| 4,809,706 A | * | 3/1989 | Watson et al. | 128/914 |
| 4,854,574 A | * | 8/1989 | Larson et al. | 128/200.24 |
| 4,973,047 A | * | 11/1990 | Norell | 482/13 |
| 5,522,380 A | * | 6/1996 | Dwork | 128/200.23 |
| 5,547,440 A | * | 8/1996 | Rubens et al. | 482/13 |
| 6,004,277 A | * | 12/1999 | Maharaj et al. | 600/532 |
| 6,135,107 A | * | 10/2000 | Mault | 128/204.23 |
| 6,138,673 A | * | 10/2000 | Shepherd | 128/203.15 |
| 6,167,880 B1 | * | 1/2001 | Gonda et al. | 128/200.14 |
| 6,309,360 B1 | * | 10/2001 | Mault | 128/200.24 |

* cited by examiner

*Primary Examiner*—Glenn K. Dawson
*Assistant Examiner*—Michael G. Mendoza

(57) ABSTRACT

A breathing support system comprises a housing, a plate with a central aperture forming an annular bearing surface and with peripheral air passageways and a cap with a base and a wall slidably extending into the distal region. Air ports have a tubular guide extending proximally from the base. A valve assembly includes a disc formed with a periphery selectively positionable in contact with the bearing surface and passageways and also includes a thin rod with a distal end adjustably received within the guide. A resilient member is positioned between the base and plate urging the base and cap distally and the disc into contact with the bearing surface and passageways. An exhaust valve adapted to allow the exhaling of air is located on an upper radial extent of an intermediate region of the housing. A primary port is adapted to receive and support a bottle of primary medication.

5 Claims, 3 Drawing Sheets

FIG 3
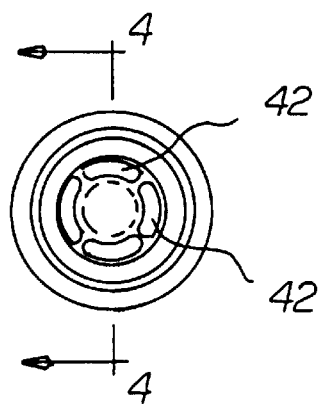
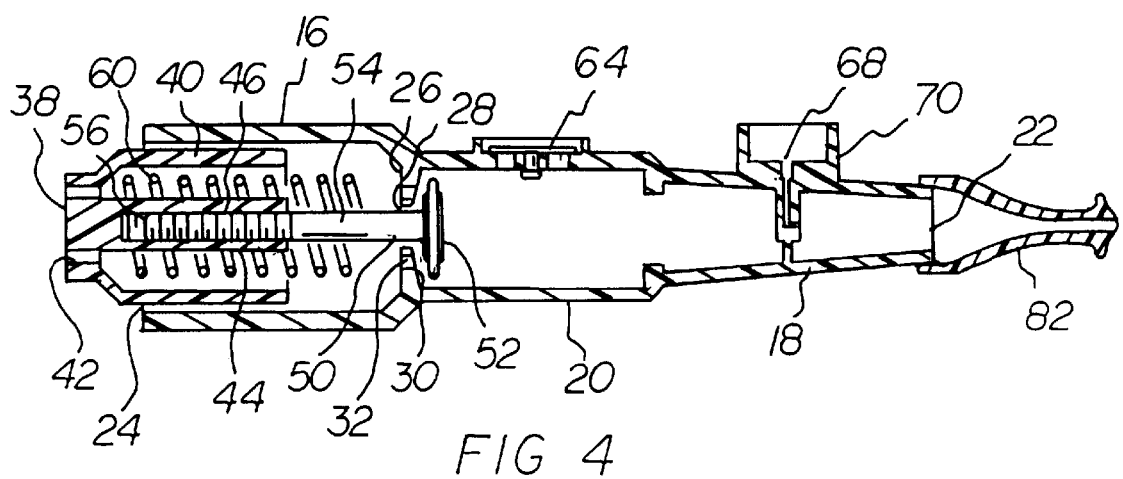
FIG 4

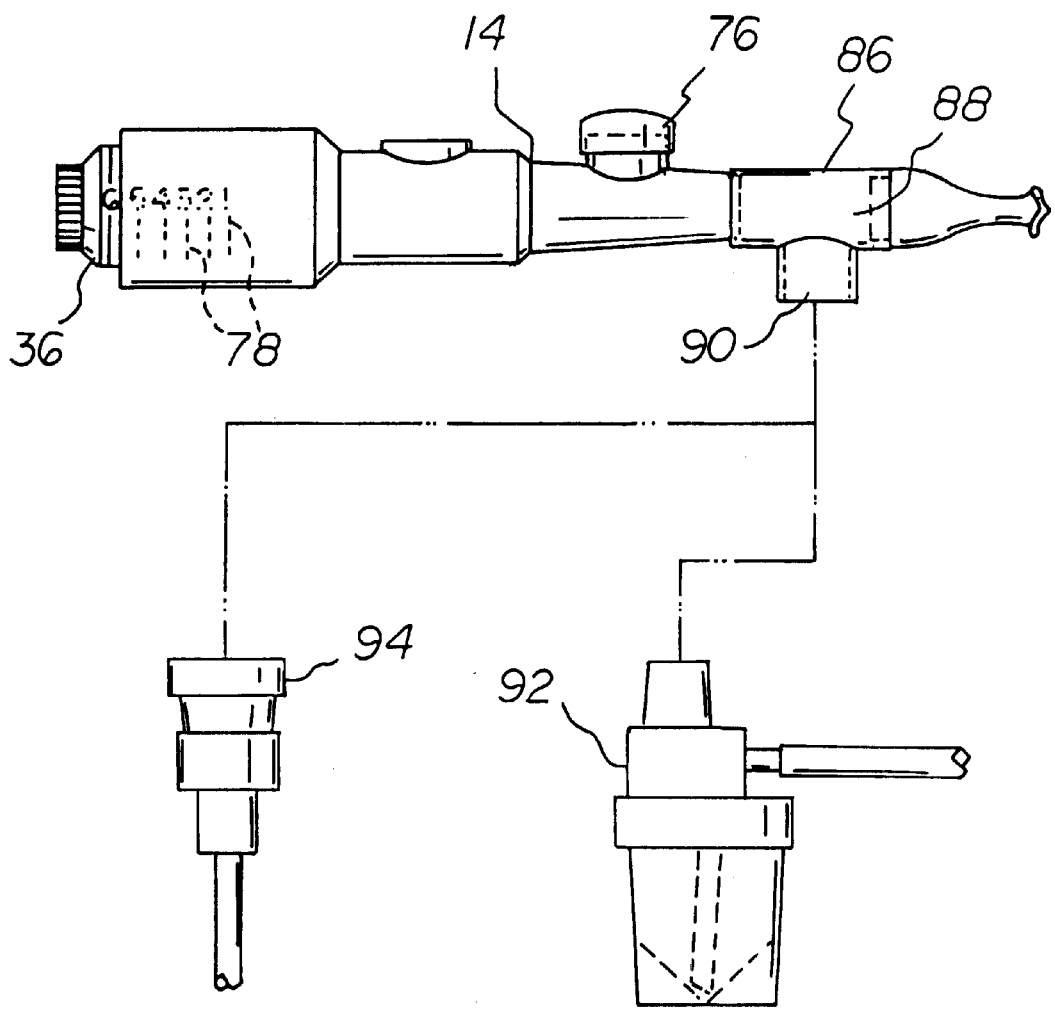

MULTI-FUNCTION ORAL BREATHING SUPPORT SYSTEM

BACKGROUND OF THE INVENTION

1. Field of the Invention

The present invention relates to a multi-function oral breathing support system and more particularly pertains to providing inhaled medication and exercise to the lungs of a patient.

2. Description of the Prior Art

The use of inhalers of known designs and configurations is known in the prior art. More specifically, inhalers of known designs and configurations previously devised and utilized for the purpose of providing medication and/or exercise to the lungs of a user through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,040,527 to Larson, et al discloses a metered dose inhalation unit with slide means. U.S. Pat. No. 6,039,042 to Sladek discloses a portable chamber for meter dose inhaler dispenser. U.S. Pat. No. 5,522,380 to Dwork discloses a metered dose medication adaptor with improved incentive spirometer. U.S. Pat. No. 5,899,832 to Hougen discloses a compact lung exercising device. U.S. Pat. No. 4,207,884 to Isaacson discloses a pressure controlled breathing apparatus. Lastly, U.S. Pat. No. 4,259,952 to Chernack et al. discloses a dual valve for respiratory device.

While these devices fulfill their respective, particular objectives and requirements, the aforementioned patents do not describe a multi-function oral breathing support system that allows providing inhaled medication and exercise to the lungs of a patient.

In this respect, the multi-function oral breathing support system according to the present invention substantially departs from the conventional concepts and designs of the prior art, and in doing so provides an apparatus primarily developed for the purpose of providing inhaled medication and exercise to the lungs of a patient.

Therefore, it can be appreciated that there exists a continuing need for a new and improved multi-function oral breathing support system which can be used for providing inhaled medication and exercise to the lungs of a patient. In this regard, the present invention substantially fulfills this need.

SUMMARY OF THE INVENTION

In view of the foregoing disadvantages inherent in the known types of inhalers of known designs and configurations now present in the prior art, the present invention provides an improved multi-function oral breathing support system. As such, the general purpose of the present invention, which will be described subsequently in greater detail, is to provide a new and improved multi-function oral breathing support system and method which has all the advantages of the prior art and none of the disadvantages.

To attain this, the present invention essentially comprises a housing has a cylindrical distal region of a first length with a large diameter. The housing also has a frusto-conical proximal region of a second length with a small diameter. Between the distal region and the proximal region, the housing has a cylindrical intermediate region of a third length with an intermediate diameter. The second length is of an extended length being greater than the first length and greater than the third length but less than the sum of the first and third lengths. The proximal region is formed with an open circular output end. The distal region is formed with an open circular input end. A circular plate is formed adjacent to the interface of the distal and intermediate regions. A central aperture forms an annular bearing surface proximally and peripheral air passageways are there around. The system has a common central axis through the proximal and distal and intermediate regions and the input and output ends and the central aperture. Next provided is a generally cup-shaped cap. The cap has a circular base and an integrally formed cylindrical wall slidably received through the input end and extending into the distal region of the housing. The base has an annular array of air ports with a tubular guide extending proximally from the base. The tubular guide is formed with internal threads. A valve assembly is next provided. The valve assembly includes a circular disc formed with a periphery selectively positionable in contact with the bearing surface and passageways for precluding the passage of air through the plate and selectively positionable out of contact with the bearing surface and passageways for allowing the passage of air through the air ports and passageways and output end. The valve assembly also includes a thin rod with a distal end formed with external threads adjustably received within the guide. Next provided is a coil spring positioned between the base and plate urging the base and cap distally and the disc into contact with the bearing surface and passageways. The coil spring is adapted to vary the amount of pressure required to allow passage of air through the cap into the housing by the inhaling at the output end by a patient. Such pressure is variable as a function of the rotational orientation of the guide and cap with respect to the rod and valve assembly. An elastomeric exhaust valve is fabricated of a soft resilient elastomeric material located on an upper radial extent of the intermediate region of the housing. The exhaust valve is adapted to allow the exhaling of air to exterior of the housing by a patient independent of the pressure of the exhaling. Next provided is a primary port on an upper radial extent of the proximal region of the housing. The upper radial extent of the proximal region of the housing is configured with an upstanding support adapted to receive and support a bottle of primary medication and has a downwardly extending nozzle extending through the primary port. Depressing of the bottle will dispense a premetered dosage of a primary medicine into the housing for being inhaled by a patient. Calibrating indicia is provided on the exterior surface of the sidewall whereby varying the distance between the guide and rod will vary the force exerted by the spring and thereby vary the inhalation force required by the patient in order to create a sufficient vacuum to pull the disc from the plate and passageways and thereby allow a patient to inhale through the housing for the receipt of medicine and exercise to the lungs. Next provided is a mouthpiece. The mouthpiece is releasably coupled to the output end of the housing. A central passageway is provided through the mouthpiece. Finally, an adapter is provided. The adapter is selectively positionable between the output end and the mouthpiece. The adapter is in a T-shaped configuration. A generally cylindrical central opening is provided through the adapter. A downwardly extending supplemental opening is adapted to couple to a container having a supplemental supply of medication for selective use by a patient.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved multi-function oral breathing support system which has all of the advantages of the prior art inhalers of known designs and configurations and none of the disadvantages.

It is another object of the present invention to provide a new and improved multi-function oral breathing support system which may be easily and efficiently manufactured and marketed.

It is further object of the present invention to provide a new and improved multi-function oral breathing support system which is of durable and reliable constructions.

An even further object of the present invention is to provide a new and improved multi-function oral breathing support system which is susceptible of a low cost of manufacture with regard to both materials and labor, and which accordingly is then susceptible of low prices of sale to the consuming public, thereby making such multi-function oral breathing support system economically available to the buying public.

Even still another object of the present invention is to provide a multi-function oral breathing support system for providing inhaled medication and exercise to the lungs of a patient.

Lastly, it is an object of the present invention to provide a new and improved breathing support system comprising a housing, a plate with a central aperture forming an annular bearing surface and with peripheral air passageways and a cap with a base and a wall slidably extending into the distal region. Air ports have a tubular guide extending proximally from the base. A valve assembly includes a disc formed with a periphery selectively positionable in contact with the bearing surface and passageways and also includes a thin rod with a distal end adjustably received within the guide. A resilient member is positioned between the base and plate urging the base and cap distally and the disc into contact with the bearing surface and passageways. An exhaust valve adapted to allow the exhaling of air is located on an upper radial extent of an intermediate region of the housing. A primary port is adapted to receive and support a bottle of primary medication.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an end elevational view taken along line 3—3 of FIG. 2.

FIG. 4 is a cross-sectional view taken along line 4—4 of FIG. 3.

FIG. 5 is an exploded elevational view of an alternate embodiment of the invention.

FIG. 6 is a cross-sectional view taken along line 6—6 of FIG. 5.

The same reference numerals refer to the same parts throughout the various Figures.

DESCRIPTION OF THE PREFERRED EMBODIMENT

Figure 1:
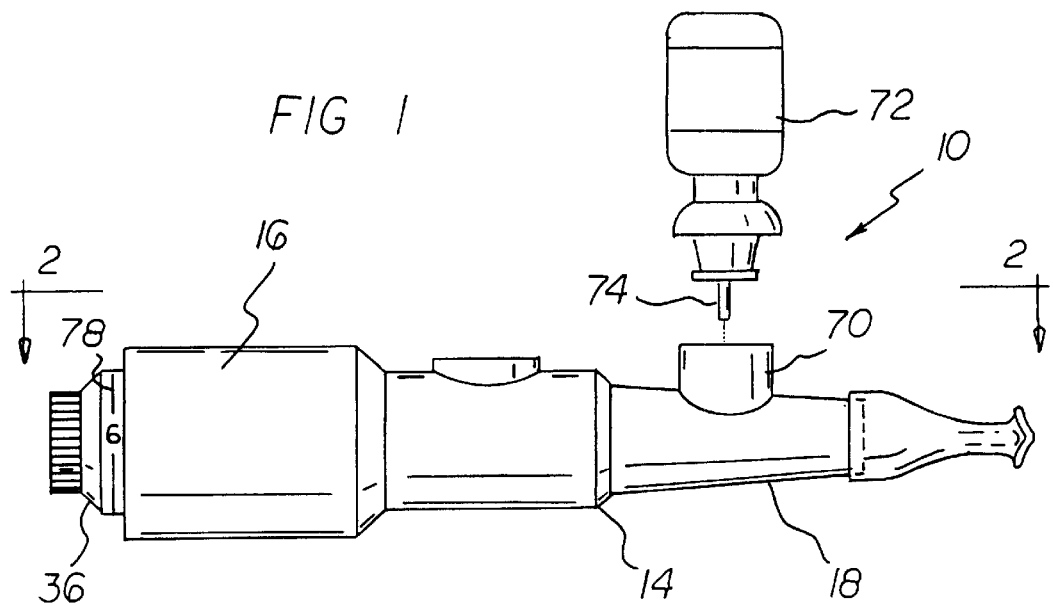
FIG. 1 is side elevational view of the multi-function oral breathing system constructed in accordance with the principles of the present invention.
Figure 2:
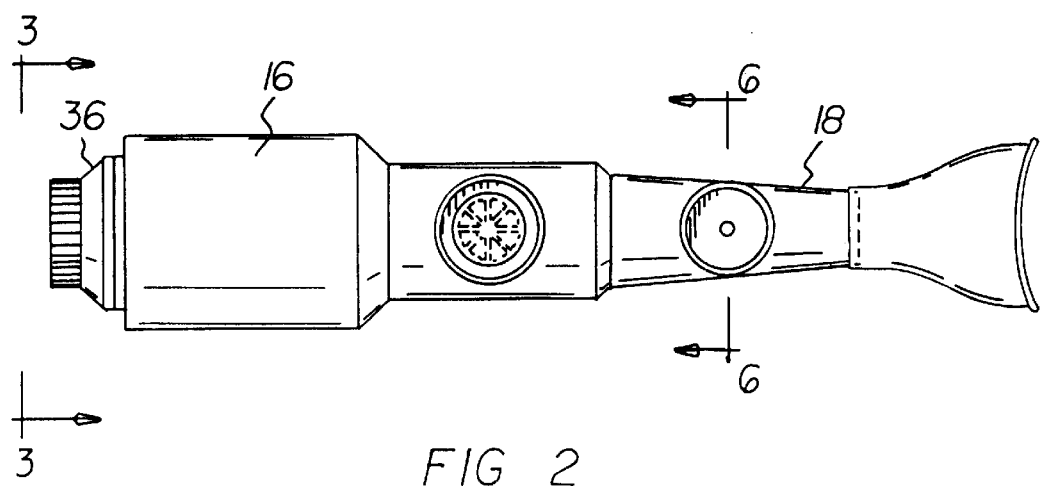
FIG. 2 is a top elevational view taken along line 2—2 of FIG. 1.

With reference now to the drawings, and in particular to FIG. 1 thereof, the preferred embodiment of the new and improved multi-function oral breathing support system embodying the principles and concepts of the present invention and generally designated by the reference numeral 10 will be described.

The present invention, the multi-function oral breathing support system 10 is comprised of a plurality of components. Such components in their broadest context include a housing, a cap, a valve assembly, a coil spring, an elastomeric exhaust valve, and a primary port. Such components are individually configured and correlated with respect to each other so as to attain the desired objective.

To attain this, the present invention essentially comprises a housing 14. The housing has a cylindrical distal region 16 of a first length with a large diameter. The housing also has a frusto-conical proximal region 18 of a second length with a small diameter. Between the distal region and the proximal region, the housing has a cylindrical intermediate region 20 of a third length with an intermediate diameter. The second length is of an extended length being greater than the first length and greater than the third length but less than the sum of the first and third lengths. The extended length provides benefits of efficiency and economy. More specifically, it is known in respiratory, that aerosol medication is more effective when the surface area-to-size ratio of such vapor particles is higher. It is better to have many small diameter particles, than fewer larger diameter particles, for the same mass of medicine administered. This is due to properties relating to cellular absorption by tissue lining the lungs. In short, many small medicine vapor droplets with a high surface area-to-volume ratio are required for more effective medicine absorption in the lungs. The extended length of the second region allows for these benefits.

The proximal region is formed with an open circular output end 22. The distal region is formed with an open circular input end 24. A circular plate 26 is formed adjacent to the interface of the distal and intermediate regions. A central aperture 28 forms an annular bearing surface 30 proximally and peripheral air passageways 32 are there around. The system has a common central axis through the proximal and distal and intermediate regions and the input and output ends and the central aperture.

Next provided is a generally cup-shaped cap 36. The cap has a circular base 38 and an integrally formed cylindrical wall 40 slidably received through the input end and extending into the distal region of the housing. The base has an annular array of air ports 42 with a tubular guide 44 extending proximally from the base. The tubular guide is formed with internal threads 46.

A valve assembly 50 is next provided. The valve assembly includes a circular disc 52 formed with a periphery selectively positionable in contact with the bearing surface and passageways for precluding the passage of air through the plate and selectively positionable out of contact with the bearing surface and passageways for allowing the passage of air through the air ports and passageways and output end. The valve assembly also includes a thin rod 54 with a distal end formed with external threads 56 adjustably received within the guide. The area between the proximal and intermediate regions is of a diameter less than the disc to preclude excess movement of the valve assembly toward the output end.

Next provided is a coil spring 60 or other resilient member positioned between the base and plate urging the base and cap distally and the disc into contact with the bearing surface and passageways. The coil spring is adapted to vary the amount of pressure required to allow passage of air through the cap into the housing by the inhaling at the output end by a patient. Such pressure is variable as a function of the rotational orientation of the guide and cap with respect to the rod and valve assembly.

An exhaust valve 64 is fabricated of a soft resilient elastomeric material, preferably latex, located on an upper radial extent of the intermediate region of the housing. The exhaust valve is adapted to allow the exhaling of air to exterior of the housing by a patient independent of the pressure of the exhaling. It is supported at its center with air passages there around.

Next provided is a primary port 68 on an upper radial extent of the proximal region of the housing. The upper radial extent of the proximal region of the housing is configured with an upstanding support 70 adapted to receive and support a bottle 72 of primary medication. The preferred bottle is an MDI canister for dispensing metered dosages of medication in a conventional manner. The canister has a downwardly extending metal nozzle 74 extending through the primary port. Depressing of the bottle will thus dispense a premetered dosage of a primary medicine into the housing for being inhaled by a patient. A cap 76 fabricated of an elastomer, such as rubber or latex, is positionable over the port when such port is not in use.

Calibrating indicia 78 is provided on the exterior surface of the sidewall whereby varying the distance between the guide and rod will vary the force exerted by the spring and thereby vary the inhalation force required by the patient in order to create a sufficient vacuum to pull the disc from the plate and passageways and thereby allow a patient to inhale through the housing for the receipt of medicine and exercise to the lungs.

Next provided is a mouthpiece 82. The mouthpiece is releasably coupled to the output end of the housing. A central passageway is provided through the mouthpiece.

Finally, an adapter 86 is provided. The adapter is selectively positionable between the output end and the mouthpiece. The adapter is in a T-shaped configuration. A generally cylindrical central opening 88 is provided through the adapter. A downwardly extending supplemental opening 90 is adapted to couple to a nebulizer or other container 92 having a supplemental supply of medication, as for example a saline solution, for selective use by a patient, as for lung irrigation. An alternate adapter 94 allows for coupling to a supply of oxygen.

The present invention thus allows for nebulized aerosol medications that are non-metered dose released. A T-shaped adapter, a T-piece, can be fitted between the unit and its mouthpiece. A nebulizer can be fitted to the bottom of this T-piece. Unlike most nebulized treatments that allow the T-piece to remain open on one end, this invention closes that T-piece system. Therefore, much less nebulized medication is lost to the air. This saves money on medicine. The nature of the invention allows the nebulized particles to be forced deep into the lungs where they are more effective, in much the same way as the MDI medication penetrates the lungs deeper with this product. The nebulizer unit can be filled with plain saline solution as well as medication.

In some instances, a doctor may prescribe combining both MDI and nebulizer/saline treatments simultaneously. The present invention has the ability to do this. As an oxygen incentive device, the T-piece adapter may also accept an adapter that allows oxygen tubing to connect to it. This incentive device is powerful, and can maximize the benefit of such oxygen treatments by expanding the lungs and taking the oxygen deeper into the lungs.

As an MDI unit and oxygen incentive device, this invention may also allow for MDI medication to be delivered simultaneously while administering an oxygen treatment. There may be some instances where an MDI medication may make an oxygen treatment more effective. This is true if the MDI medication is a bronchiole dilator which opens up the airways of the lungs. This would allow the oxygen to penetrate far better into the lungs.

This invention prevents the patient from having too fast an inspiration rate upon metered dosage administration. This invention, because of its almost infinite resistance settings, allows the patient to titrate dosage of the aerosol medication.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A multi-function oral breathing support system for providing inhaled medication and exercise to the lungs of a patient comprising, in combination:

a one piece housing having a cylindrical distal region of a first length with a large diameter and a frusto-conical proximal region of a second length with a small diameter and a cylindrical intermediate region of a third length with an intermediate diameter there between, the second length of an extended length being greater than the first length and greater than the third length but less than the sum of the first and third lengths, the proximal region being formed with an open circular output end and the distal region being formed with an open circular input end, a circular plate formed adjacent to the interface of the distal and intermediate regions with a central aperture forming an annular bearing surface proximally and with peripheral air passageways there around, the system having a common central axis through the proximal and distal and intermediate regions and the input and output ends and the central aperture;

a generally cup-shaped cap with a circular base and an integrally formed cylindrical sidewall slidably received through the input end and extending into the distal region of the housing, the base having an annular array of air ports with a tubular guide extending proximally from the base, the tubular guide being formed with internal threads;

a valve assembly including a circular disc formed with a periphery selectively positionable in contact with the bearing surface and passageways for precluding the passage of air through the plate and selectively positionable out of contact with the bearing surface and passageways for allowing the passage of air through the air ports and passageways and output end, the valve assembly also including a thin rod with a distal end formed with external threads adjustably received within the guide;

a coil spring positioned between the base and plate urging the base and cap distally and the plate into contact with the bearing surface and passageways and adapted to vary the amount of pressure required to allow passage of air through the cap into the housing by the inhaling at the output end by a patient, such pressure being variable as a function of the rotational orientation of the guide and cap with respect to the rod and valve assembly;

an elastomeric exhaust valve fabricated of a soft resilient elastomeric material located on an upper radial extent of the intermediate region of the housing adapted to allow the exhaling of air to exterior of the housing by a patient independent of the pressure of the exhaling;

a primary port on an upper radial extent of the proximal region of the housing configured with an upstanding support adapted to receive and support a bottle of medication with a downwardly extending nozzle extending through the primary port whereby depressing of the bottle will dispense a premetered dosage of medication into the housing for being inhaled by a patient;

calibrating indicia on the exterior surface of the sidewall whereby varying the distance between the guide and rod will vary the force exerted by the spring and thereby varying the inhalation force required by the patient in order to create a sufficient vacuum to pull the disc from the plate and passageways and thereby allow a patient to inhale through the housing for the receipt of medication and exercise to the lungs;

a mouthpiece releasably coupled to the output end of the housing with a central passageway there through; and an adapter selectively positionable between the output end and the mouthpiece, the adapter being in a T-shaped configuration with a generally cylindrical central opening there through and a downwardly extending supplemental opening adapted to couple to a container having a supplemental supply of medication for selective use by a patient.

2. A breathing support system comprising:

a housing having a distal region and a frusto-conical proximal region and an intermediate there between, a plate formed adjacent to the interface of the distal and intermediate regions with a central aperture forming an annular bearing surface proximally and with peripheral air passageways there around;

a cap with a base and a wall slidably extending into the distal region, the base having an annular array of air ports with a tubular guide extending proximally from the base;

a valve assembly including a disc formed with a periphery selectively positionable in contact with the bearing surface and passageways, the valve assembly also including a thin rod with a distal end adjustably received within the guide;

a resilient member positioned between the base and plate urging the base and cap distally and the plate into contact with the bearing surface and passageways;

an exhaust valve fabricated of a soft resilient elastomeric material located on an upper radial extent of the intermediate region of the housing adapted to allow the exhaling of air; and a primary port on an upper radial extent of the proximal region of the housing adapted to receive and support a bottle of medication.

3. The system as set forth in claim 2 and further including calibrating indicia on the exterior surface of the cap.

4. The system as set forth in claim 2 and further including a mouthpiece releasably coupled to the output end of the housing.

5. The system as set forth in claim 2 and further including an adapter selectively positionable at the output end, the adapter being in a T-shaped configuration with a generally cylindrical central passageway there through and a downwardly extending supplemental port.

* * * * *